United States Patent
Almassian et al.

(10) Patent No.: US 7,456,179 B2
(45) Date of Patent: Nov. 25, 2008

(54) METHODS OF TREATING ISCHEMIC RELATED CONDITIONS

(75) Inventors: Bijan Almassian, Cheshire, CT (US); Hossein A. Ghanbari, Potomac, MD (US); Michael Lebowitz, Baltimore, MD (US); Weiying Pan, Baltimore, MD (US); Zhi-Gang Jiang, Gaithersburg, MD (US)

(73) Assignee: Panacea Pharmaceuticals, Inc., Gaithersburg, MD (US)

( * ) Notice: Subject to any disclaimer, the term of this patent is extended or adjusted under 35 U.S.C. 154(b) by 403 days.

(21) Appl. No.: 10/835,668

(22) Filed: Apr. 30, 2004
(Under 37 CFR 1.47)

(65) Prior Publication Data
US 2006/0160826 A1    Jul. 20, 2006

Related U.S. Application Data

(60) Provisional application No. 60/552,231, filed on Mar. 10, 2004, provisional application No. 60/467,473, filed on May 1, 2003.

(51) Int. Cl.
*A61K 31/4965* (2006.01)
*A61K 31/44* (2006.01)
*A61K 31/426* (2006.01)
*A61K 31/4172* (2006.01)

(52) U.S. Cl. .................... 514/252.1; 514/357; 514/365; 514/400

(58) Field of Classification Search .................. None
See application file for complete search history.

(56) References Cited

U.S. PATENT DOCUMENTS

| 5,721,259 | A | 2/1998 | Sartorelli et al. |
| 6,911,460 | B2 * | 6/2005 | King et al. .................. 514/352 |
| 2002/0188011 | A1 | 12/2002 | King et al. |
| 2004/0038890 | A1 * | 2/2004 | Aiyar et al. .................. 514/12 |

FOREIGN PATENT DOCUMENTS

| WO | WO 2004/099371 A2 | 11/2004 |
| WO | WO 2004099371 A2 * | 11/2004 |

* cited by examiner

*Primary Examiner*—Brian-Yong S Kwon
(74) *Attorney, Agent, or Firm*—M. Elisa Lane

(57) ABSTRACT

The present invention relates to methods of treating ischemia-related conditions by administering to a patient in need of such methods certain thiosemicarbazone compounds. Preferred embodiments of the present invention relates to methods of treating specific ischemia-related conditions, including but not limited to Alzheimer's disease, Parkinson's disease, Coronary artery bypass graft surgery, Global cerebral ischemia due to cardiac arrest, focal cerebral infarction, cerebral hemorrhage, hemorrhage infarction, hypertensive hemorrhage. hemorrhage due to rupture of intracranial vascular abnormalities, subarachnoid hemorrhage due to rupture of intracranial arterial aneurysms, hypertensive encephalopathy, carotid stenosis or occlusion leading to cerebral ischemia, cardiogenic thromboembolism, spinal stroke and spinal cord injury, diseases of cerebral blood vessels: e.g., atherosclerosis, vasculitis, Macular degeneration, myocardial infarction, cardiac ischemia and superaventicular tachyarrhytmia.

1 Claim, 11 Drawing Sheets

FIGURE 1
(A). PAN-811
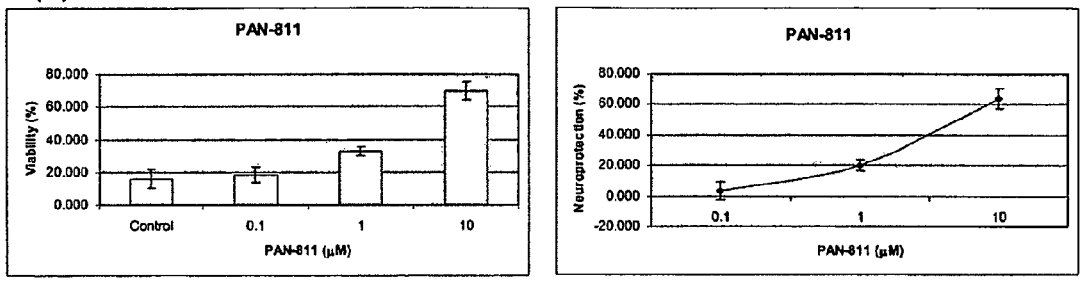
(B). Vitamin E
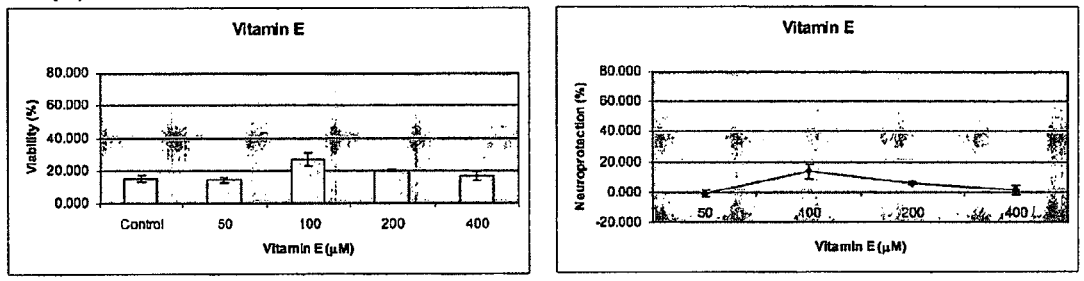
(C). Lipoic Acid
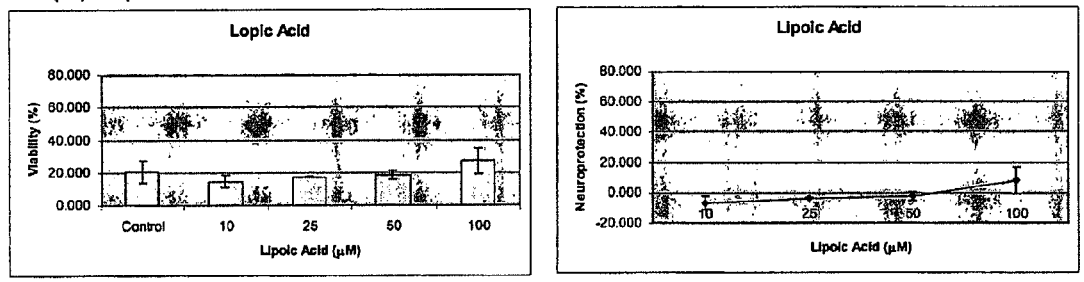
(D). Ginkgo Biloba
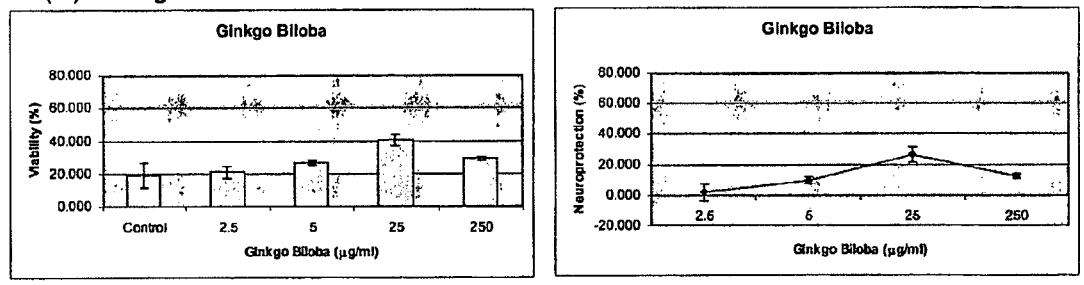

Figure 2
(A). PAN-811 reduces $H_2O_2$-induced ROS generation in neuronal cells.
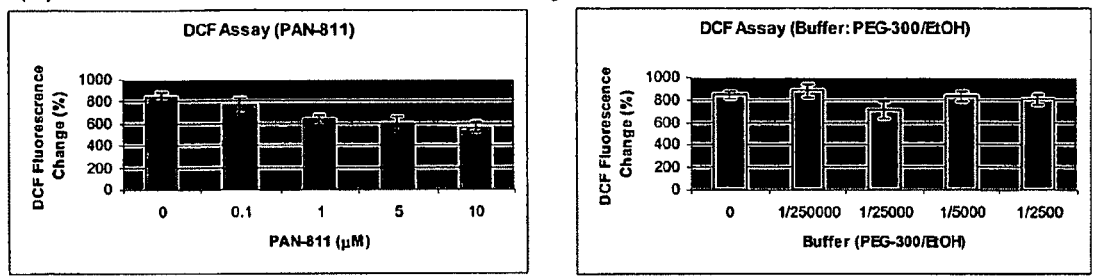
(B). PAN-811 reduces the basal level of ROS generation in neuronal cells.
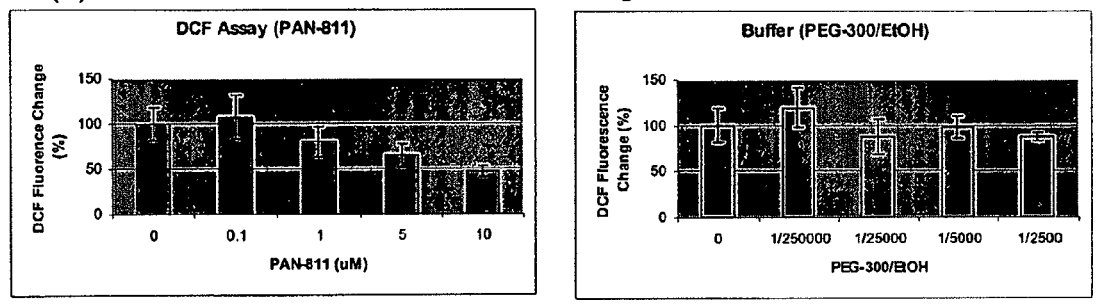

Figure 1: *Neurotoxicity of PAN-811.* Cortical neurons were treated with the indicated doses of PAN-811 for 24 hours. Cell viability was determined by thee MTT assay.

Figure 2: PAN-811 protects against toxicity of ischemia (ISC, 3hrs), glutamate (Glut, 100 µM), staurosporine (ST, 1 µM) and veratridine (Ver, 10 µM). Primary cortical neuron cultures. Neurons were pretreated at with 10 µM PAN-811 for 24 hrs, then treated with different stimuli. Cell viability was measured with MTT assay 24 hrs later. Cell viability is expressed as % of untreated Control (CTL).

Figure 10
3-AP in EtOH
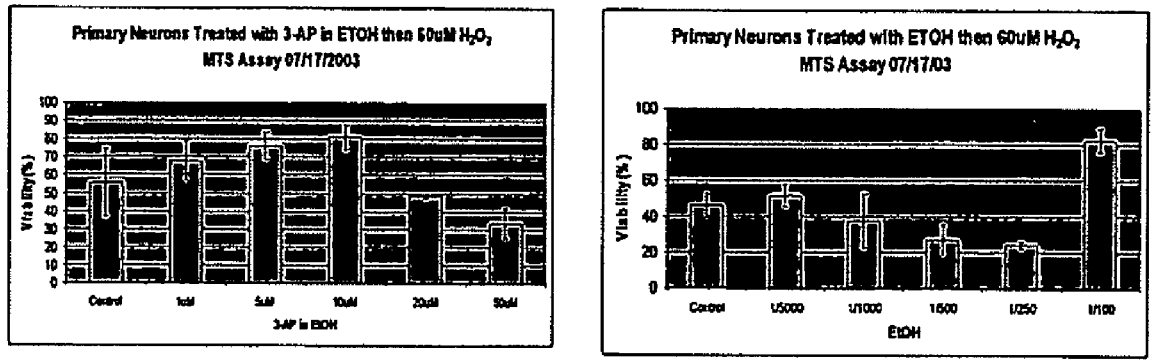
3-AP in DMSO
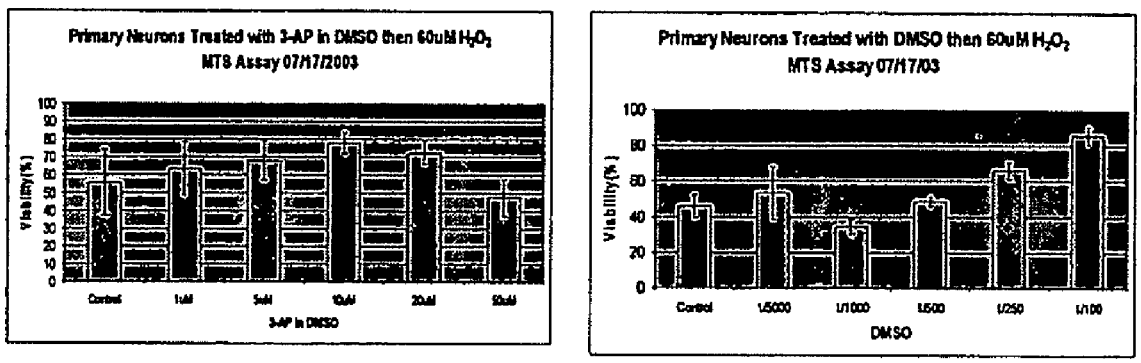
3-AP in PEG-300/EtOH
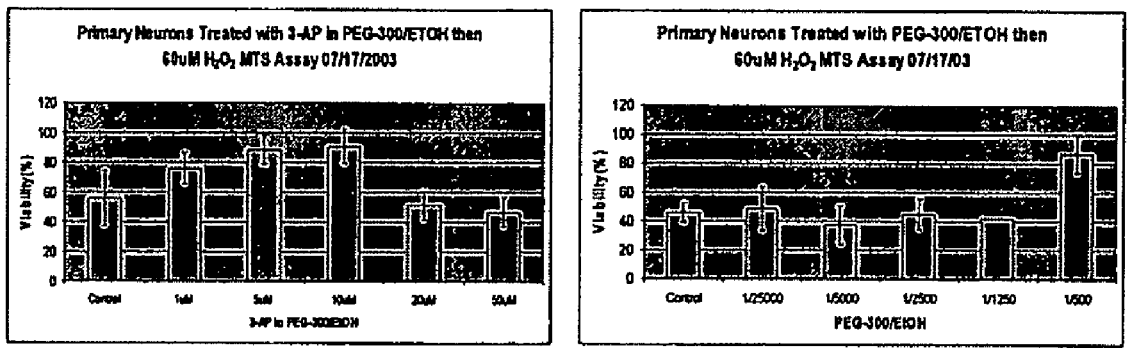

Figure 11
3-AP in EtOH
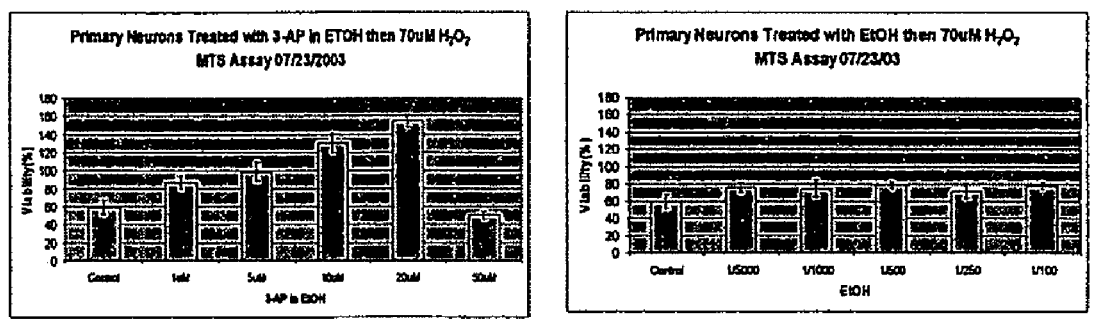
3-AP in DMSO
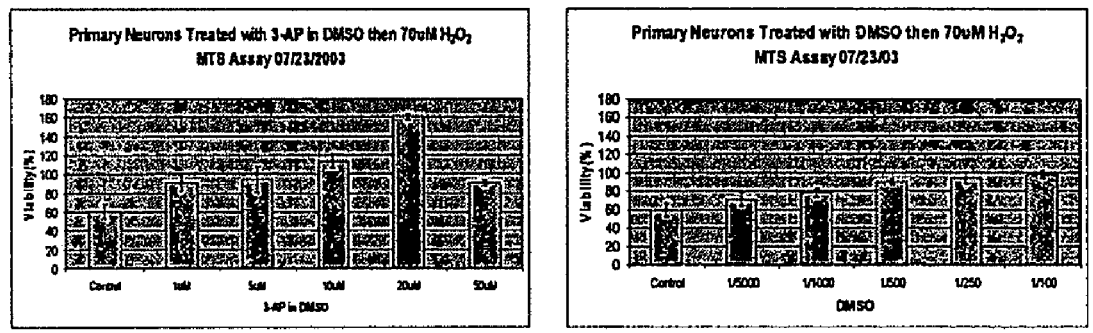
3-AP in PEG/EtOH
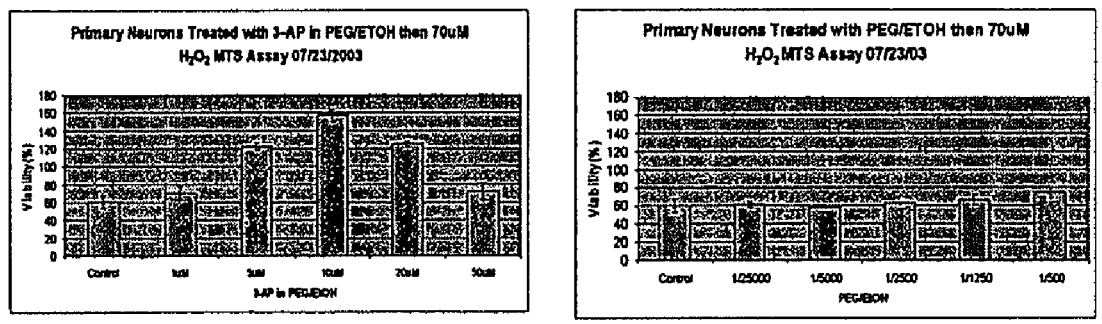

METHODS OF TREATING ISCHEMIC RELATED CONDITIONS

PRIORITY

The present application claims priority to U.S. Provisional Application Nos. 60/467,473, filed May 1, 2003 and 60/552,231, filed Mar. 10, 2004.

FIELD OF THE INVENTION

The present invention relates to methods of treating ischemia-related diseases and disorders, including neuronal and cardiac diseases due to sudden loss of oxygen, as well as degenerative diseases, such as, Alzheimer's disease.

BACKGROUND OF THE INVENTION

The central nervous system (CNS) is comprised of the spinal cord, brain and retina, and contains trillions of nerve cells (neurons) that form networks capable of performing exceedingly complex functions. CNS neurons require energy to survive and perform their physiological functions, and it is generally recognized that the only source of energy for CNS neurons is the glucose and oxygen delivered by the blood. If the blood supply to all or any portion of the CNS is shut off, thereby depriving neurons of both oxygen and glucose (a condition known as ischemia), the deprived neurons rapidly degenerate. This condition of inadequate blood flow is commonly known in clinical neurology as a "stroke." If only the oxygen supply to the brain is interrupted, for example in asphyxia, suffocation or drowning, the condition is referred to as "hypoxia". If only the glucose supply is disrupted, for example when a diabetic takes too much insulin, the condition is called "hypoglycemia". All of these conditions involve energy deficiency and are recognized in clinical medicine as potential causes of brain damage. In the following text, the terms "energy deficiency" or "ischemia" are used interchangeably to refer to any of these conditions that entail CNS energy impairment.

In recent years, neuroscientists have made considerable progress in understanding the mechanism by which energy deficiency leads to neuronal degeneration. It has been learned that glutamate, which functions under normal and healthy conditions as an important excitatory neurotransmitter in the CNS, can exert neurotoxic properties referred to as "excitotoxicity" if ischemic conditions arise. Normally, glutamate is confined intracellularly, and is only released from a nerve cell at a synaptic junction in tiny amounts, for purposes of contacting a glutamate receptor on an adjacent neuron; this transmits a nerve signal to the receptor-bearing cell. Under healthy conditions, the glutamate released into the extracellular fluid in a synaptic junction is transported back inside a neuron within a few milliseconds, by a highly efficient transport process.

The excitotoxic potential of glutamate is held in check as long as the transport process is functioning properly. However, this transport process is energy dependent, so under ischemic conditions (energy deficiency), glutamate transport becomes incompetent, and glutamate molecules which have been released for transmitter purposes accumulate in the extracellular synaptic fluid. This brings glutamate continually in contact with its excitatory receptors, causing these receptors to be excessively stimulated, a situation which can literally cause neurons to be excited to death. Two additional factors complicate and make matters worse: (1) overstimulated neurons begin to release excessive quantities of glutamate at additional synaptic junctions; this causes even more neurons to become overstimulated, drawing them into a neurotoxic cascade that reaches beyond the initial zone of ischemia; and, (2) overstimulated neurons begin utilizing any available supplies of glucose or oxygen even faster than normal, which leads to accelerated depletion of these limited energy resources and further impairment of the glutamate transport process. Thus, energy deficiency conditions such as stroke, cardiac arrest, asphyxia, hypoxia or hypoglycemia cause brain damage by a compound mechanism; the initial causative mechanism is the ischemia itself, but this leads to failure of the glutamate transport system and a cascade of glutamate-mediated excitotoxic events that are largely responsible for the ensuing brain damage.

In addition to the conditions already mentioned, it has recently become recognized that various defects in the neuron's ability to utilize energy substrates (glucose and oxygen) to maintain its energy levels can also trigger an excitotoxic process leading to death of neurons. It has been postulated that this is the mechanism by which neuronal degeneration occurs in neurological diseases such as Alzheimer's dementia, Parkinsonism, Huntington's Chorea and amyotrophic lateral sclerosis. For example, evidence for defective intracellular energy metabolism has been found in samples of tissue removed by biopsy from the brains of patients with Alzheimer's disease and this has been proposed as the causative mechanism that triggers an unleashing of the excitotoxic potential of glutamate with death of neurons in Alzheimer's disease thereby being explained by an energy-linked excitotoxic process. Evidence for an intrinsic defect in intracellular energy metabolism has also been reported in Parkinsonism and Huntington's Chorea. Thus, rational therapeutic strategies for preventing neuronal degeneration in these disorders would include methods that correct energy deficiency or that prevent excitotoxic neuronal degeneration.

Neurodegenerative diseases are a group of disorders characterized by changes in the normal neuronal function, leading, in most cases, to neuronal death (most of these diseases are associated, especially in late stages, with severe neuronal loss). In most instances, the etiological causes are unknown and they have a progressive development. The end point of neurodegenerative diseases, without exception, extracts an enormous emotional, physical and financial strain on the affected individual and wider community.

The most consistent risk factor for developing a neurodegenerative disorder, especially Alzheimer's disease or Parkinson's disease, is increasing age. Over the past century, the growth rate of the population aged 65 and beyond in industrialized countries has far exceeded that of the population as a whole. Thus, it can be anticipated that, over the next generations, the proportion of elderly citizens will double, and, with this, possibly the proportion of persons suffering from some kind of neurodegenerative disorder. This prediction is at the center of growing concerns in the medical community and among lawmakers, for one can easily foresee the increasing magnitude of emotional, physical, and financial burdens on patients, caregivers, and society that are related to these disabling illnesses. Compounding the problem is the fact that while, to date, several approved drugs do, to some extent, alleviate symptoms of several neurodegenerative diseases, their chronic use is often associated with debilitating side effects, and none seems to stop the progression of the degenerative process. In keeping with this, the development of effective preventive or protective therapies has been impeded by the limitations of our knowledge of the causes and the mechanisms by which neurons die in neurodegenerative diseases. Despite this bleak outlook, several neurobiological breakthroughs have brought closer than ever the day when the secrets of several neurodegenerative disorders will be unlocked and effective therapeutic strategies will become available.

Significant advances have been made in developing methods for preventing or reducing the neuronal damage associated with CNS ischemia. The most active research in this area involves methods of inhibiting excitatory activity at glutamate receptors, using receptor-specific antagonist drugs (in pharmaceutical terminology, a drug that occupies and blocks a certain receptor on a cell surface without triggering activity at that receptor is called an antagonist of that receptor). The glutamate receptors that can mediate excitotoxic neuronal degeneration are broadly divided in two broad categories designated as "NMDA" and "non-NMDA" receptors. NMDA receptors are named after N-methyl-D-aspartate, a drug which does not naturally occur inside the brain, but which was discovered to bind strongly to certain glutamate receptors, which were therefore called "NMDA receptors." The "non-NMDA" class of glutamate receptors has more recently been subdivided into two distinct categories, referred to as KA (kainic acid) receptors and AMPA receptors (formerly called QUIS receptors).

It has been demonstrated repeatedly that NMDA receptor antagonists can protect against CNS ischemic neuronal degeneration in both in vitro tests and a number of in vivo animal models; however, various items of more recent evidence suggest that NMDA antagonists may be ineffective in one major type of ischemia known as "global ischemia" and provide only partial protection in the other major type of ischemia, known as "focal" ischemia. Moreover, it appears that NMDA antagonists must be administered immediately at the onset of ischemia to provide significant protection. Experimental evidence pertaining to non-NMDA antagonists is more limited, but the few in vivo animal studies available suggest that these agents may provide significant protection against ischemic neuronal degeneration, even when applied after the ischemic event.

Despite claims that either NMDA or non-NMDA antagonists, used alone, can provide substantial protection against CNS ischemia, a growing body of evidence suggests that the degree of protection afforded by either NMDA or non-NMDA antagonists, alone, is relatively modest A significant limitation of glutamate receptor antagonists as neuroprotectants against ischemic neurodegeneration is that they only insulate the neuron temporarily against degeneration; they do not do anything to correct the energy deficit, or to correct other derangements that occur secondary to the energy deficit. Therefore, although these agents do provide some level of protection against ischemic neurodegeneration in experimental animal models, the protection is only partial and in some cases may only be a delay in the time of onset of degeneration, as mentioned above. However, it is important to note that a delay in the onset of degeneration may be extremely valuable, if there are other drugs or procedures that can be applied during the delay interval to provide additional and/or lasting protection.

One critical factor which is not adequately addressed in most ischemia research concerns the timing of drug administration in relation to the injurious (ischemic) event. This is an important consideration; although some ischemic events can be predicted (for example, involving open-heart surgery), the great majority cannot, and in most cases, therapy can only be initiated during or after an ischemic event. Since CNS cells begin to degenerate very rapidly after the onset of ischemia, there is clearly a need for new neuroprotective methods that are effective when applied after CNS neurons have begun to degenerate.

Another important consideration is whether the ischemia is only transient (e.g. during an episode of cardiac arrest) or is permanent (e.g. following thrombotic or embolic occlusion of CNS blood vessels). If the ischemia is transient, the blood supply carrying oxygen and glucose to the CNS is restored immediately after the event and drugs that prevent neuronal degeneration or promote recovery from the ischemic insult can reach the ischemic tissue through the blood circulation.

If the blood supply to a region of the brain is permanently blocked by a clot, it is not possible by current methods to prevent neuronal degeneration in the center of the ischemic area, because the ischemic tissue is permanently deprived of oxygen and glucose and drugs cannot be delivered to the ischemic tissue through the blocked blood vessel. However, there is a large tissue zone, known as the penumbra, at the circumferential margin of the ischemic area which receives blood from adjoining CNS regions, and this tissue zone is a potential target for drug therapy. Also, drugs that dissolve blood clots (thrombolytic agents, such as streptokinase and tissue plasminogen activator), which currently are being used to treat heart attack victims, are being tested and developed for restoring blood supply to the CNS after a stroke. When such drugs become widely available for CNS use in humans, it will be possible to use them to open the blood vessel so that the ischemic CNS tissue can receive not only oxygen and glucose but also the drugs disclosed herein which can prevent neuronal degeneration or promote recovery from the ischemic insult.

Finally, there are special situations such as thrombotic occlusion of the major artery supplying blood to the retina of the eye, which can be aided by the drugs disclosed herein. When this blood vessel is occluded, it is possible to deliver the drugs of this invention to the ischemic retina by injecting the drug directly into the vitreous of the eye (i.e., into the clear fluid inside the eyeball). The drug can rapidly diffuse from the vitreous into the retina.

The development of therapeutic agents capable of preventing or treating the disease/disorder consequences of ischemic events, whether acute or chronic, would be highly desirable.

SUMMARY OF THE INVENTION

The present invention relates to methods of treating ischemia-related conditions by administering to a patient in need of such treatment a compound of Formula I, or a prodrug thereof:

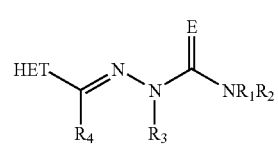

Formula I wherein

E is oxygen, sulfur, NH or N—$C_{1-6}$alkyl;

$R_1$, $R_2$, $R_3$, and $R_4$ are independently selected from the group consisting of hydrogen, optionally substituted alkyl, optionally substituted alkenyl, optionally substituted alkynyl, optionally substituted cycloalkyl, optionally substituted haloalkyl, optionally substituted aryl, optionally substituted aminoalkyl, optionally substituted hydroxyalkyl, optionally substituted alkoxyalkyl, and optionally substituted alkanoyl, or NR$_1$R$_2$ taken in combination form a 3 to 7 member ring which may comprise 0, 1, or 2 additional ring heteroatoms selected from N, O, and S; and HET is an optionally substituted 5- to 7-membered heteroaryl residue which comprises between 1 and 4 ring heteroatoms selected from N, O, or S.

Preferred embodiments relate to compositions which are used in the methods of the present invention wherein HET is a residue of the formula:

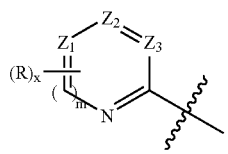

wherein m is 0 or 1;

Z$_1$, Z$_2$, and Z$_3$ are independently selected from N, O, S, or CR, when m is 0, or Z$_1$, Z$_2$, and Z$_3$ are independently selected from N or CR, when m is 1;

R is independently selected at each occurrence from the group consisting of hydrogen, halide, hydroxy, thiol, amino, hydroxyamino, mono-C$_{1-8}$alkylamino, di(C$_{1-8}$alkyl)amino, C$_{1-8}$alkoxy, C$_{1-8}$alkyl, C$_{2-8}$alkenyl, and C$_{2-8}$alkynyl; and x is an integer from 0 to 4.

Still more preferred embodiments include the use of compositions wherein HET is a residue selected from the group consisting of optionally substituted pyridyl, optionally substituted pyrazinyl, pyrimidinyl, pyrrolyl, imidazolyl, triazolyl, oxazolyl, thioxazolyl; and R$_1$, R$_2$, R$_3$, and R$_4$ are independently selected from the group consisting of hydrogen, C$_{1-8}$alkyl, C$_{2-8}$alkenyl, C$_{2-8}$alkynyl, C$_{3-8}$cycloalkyl, C$_{1-8}$haloalkyl, C$_{6-10}$aryl, amino-C$_{1-8}$alkyl, hydroxy-C$_{1-8}$alkyl, C$_{1-8}$alkoxy-C$_{1-8}$alkyl, and C$_{1-8}$alkanoyl, or NR$_1$R$_2$ taken in combination form a 3 to 7 member ring which may comprise 0, 1, or 2 additional ring heteroatoms selected from N, O, and S.

Another embodiment of the present invention relates to methods of treating ischemia-related conditions by administering to a patient in need of such treatment a compound of Formula II, or a prodrug thereof:

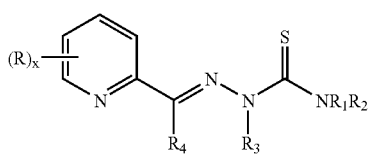

Formula II wherein

R, R$_1$, R$_2$, R$_3$, and R$_4$ are independently selected from the group consisting of hydrogen, optionally substituted alkyl, optionally substituted alkenyl, optionally substituted alkynyl, optionally substituted cycloalkyl, optionally substituted haloalkyl, optionally substituted aryl, optionally substituted aminoalkyl, optionally substituted hydroxyalkyl, optionally substituted alkoxyalkyl, and optionally substituted alkanoyl, or NR$_1$R$_2$ taken in combination form a 3 to 7 member ring which may comprise 0, 1, or 2 additional ring heteroatoms selected from N, O, and S; and x is an integer of 0 to 5.

And, more particularly wherein;

x is 0, 1, 2, or 3

R, R$_1$, R$_2$, R$_3$, and R$_4$ are independently selected from the group consisting of hydrogen, C$_{1-8}$alkyl, C$_{2-8}$alkenyl, C$_{2-8}$alkynyl, C$_{3-8}$cycloalkyl, C$_{1-8}$haloalkyl, C$_{6-10}$aryl, amino-C$_{1-8}$alkyl, hydroxy-C$_{1-8}$alkyl, C$_{1-8}$alkoxy-C$_{1-8}$alkyl, and C$_{1-8}$alkanoyl, or NR$_1$R$_2$ taken in combination form a 3 to 7 member ring which may comprise 0, 1, or 2 additional ring heteroatoms selected from N, O, and S.

Still another embodiment of the present invention relates to methods of treating ischemia-related conditions by administering to a patient in need of such treatment a compound or prodrug according to Formula III:

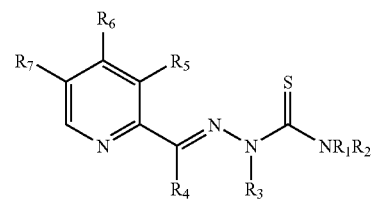

Formula III wherein

R, R$_1$, R$_2$, R$_3$, and R$_4$ are independently selected from the group consisting of hydrogen, C$_{1-8}$alkyl, C$_{2-8}$alkenyl, C$_{2-8}$alkynyl, C$_{3-8}$cycloalkyl, C$_{1-8}$haloalkyl, C$_{6-10}$aryl, amino-C$_{1-8}$alkyl, hydroxy-C$_{1-8}$alkyl, C$_{1-8}$alkoxy-C$_{1-8}$alkyl, and C$_{1-8}$alkanoyl, or NR$_1$R$_2$ taken in combination form a 3 to 7 member ring which may comprise 0, 1, or 2 additional ring heteroatoms selected from N, O, and S;

R$_6$ is hydrogen, hydroxy, amino, or C$_{1-8}$alkyl;

R$_5$ and R$_7$ are independently selected from the group consisting of hydrogen, halide, hydroxy, thiol, amino, hydroxyamino, mono-C$_{1-8}$alkylamino, di(C$_{1-8}$alkyl)amino, C$_{1-8}$alkoxy, C$_{1-8}$alkyl, C$_{2-8}$alkenyl, and C$_{2-8}$alkynyl.

A most preferred embodiment of the present invention relates to methods of treating ischemia-related conditions by administering to a patient in need of such treatment PAN 811 (3-aminopyridine-2-carboxaldehyde thiosemicarbazone) of the following formula:

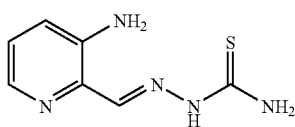

Preferred embodiments of the present invention relate to methods of treating specific ischemia-related conditions, including but not limited to Alzheimer's disease, Parkinson's disease, Coronary artery bypass graft surgery, Global cerebral ischemia due to cardiac arrest, focal cerebral infarction, cerebral hemorrhage, hemorrhage infarction, hypertensive hemorrhage. hemorrhage due to rupture of intracranial vascular abnormalities, subarachnoid hemorrhage due to rupture of intracranial arterial aneurysms, hypertensive encephalopathy, carotid stenosis or occlusion leading to cerebral ischemia, cardiogenic thromboembolism, spinal stroke and spinal cord injury, diseases of cerebral blood vessels: e.g., atherosclerosis, vasculitis, Macular degeneration, myocardial infarction, cardiac ischemia and superaventicular tachyarrhytmia.

BRIEF DESCRIPTION OF THE FIGURES

FIG. 1 contains graphic representations of cell viability (left panel) and neuroprotective capacity (right panel) after pre-treatment with PAN-811 (A) or known neuroprotectants Vitamin E (B), lipoic acid (C), or *Ginkgo Biloba* (D) and subsequent treatment with $H_2O_2$.

FIG. 2 contains graphic representations of the effects of PAN-811 on ROS generation in neuronal cells. (A); the effects of PAN-811 on $H_2O_2$-induced ROS generation in neuronal cells. (B); the effects of PAN-811 on the basal level of ROS generation in neuronal cells.

FIG. 10 are graphic representations of cell viability after pre-treatment with PAN-811 or solvent and treatment with $H_2O_2$.

FIG. 11 are graphic representations of cell viability after pre-treatment with PAN-811 or solvent and treatment with $H_2O_2$.

DETAILED DESCRIPTION OF THE INVENTION

Figure 3:
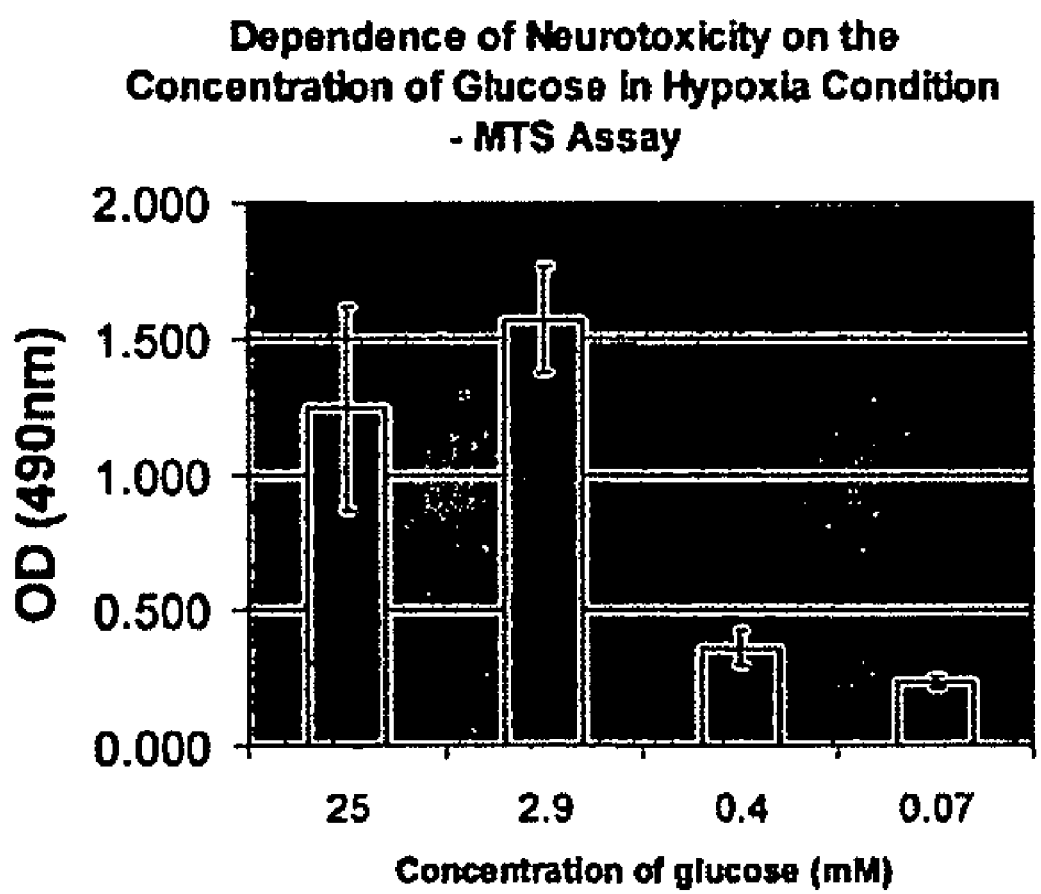
FIG. 3 is a graphic representation of the dependance of neurotoxicity on the concentration of glucose in hypoxic conditions.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Ischemia-related disorder/disease pathologies involve a decrease in the blood supply to a bodily organ, tissue or body part generally caused by constriction or obstruction of the blood vessels as for example retinopathy, acute renal failure, myocardial infarction and stroke. They can be the result of an acute event (e.g., heart attack) or a chronic progression of events (e.g., neurodegenerative disease).

The present invention relates to methods of treating ischemia-related conditions by administering to a patient in need of such treatment a compound of Formula I, or a prodrug thereof:

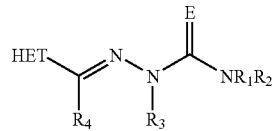

Formula I wherein

E is oxygen, sulfur, NH or N—$C_{1-6}$alkyl;

$R_1$, $R_2$, $R_3$, and $R_4$ are independently selected from the group consisting of hydrogen, optionally substituted alkyl, optionally substituted alkenyl, optionally substituted alkynyl, optionally substituted cycloalkyl, optionally substituted haloalkyl, optionally substituted aryl, optionally substituted aminoalkyl, optionally substituted hydroxyalkyl, optionally substituted alkoxyalkyl, and optionally substituted alkanoyl, or $NR_1R_2$ taken in combination form a 3 to 7 member ring which may comprise 0, 1, or 2 additional ring heteroatoms selected from N, O, and S; and HET is an optionally substituted 5- to 7-membeed heteroaryl residue which comprises between 1 and 4 ring heteroatoms selected from N, O, or S.

Preferred embodiments relate to compositions which are used in the methods of the present invention wherein HET is a residue of the formula:

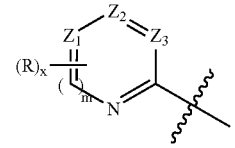

wherein m is 0 or 1;

$Z_1$, $Z_2$, and $Z_3$ are independently selected from N, O, S, or CR, when m is 0, or $Z_1$, $Z_2$, and $Z_3$ are independently selected from N or CR, when m is 1;

R is independently selected at each occurrence from the group consisting of hydrogen, halide, hydroxy, thiol, amino, hydroxyamino, mono-$C_{1-8}$alkylamino, di($C_{1-8}$alkyl)amino, $C_{1-8}$alkoxy, $C_{1-8}$alkyl, $C_{2-8}$alkenyl, and $C_{2-8}$alkynyl; and x is an integer from 0 to 4.

Still more preferred embodiments include the use of compositions wherein HET is a residue selected from the group consisting of optionally substituted pyridyl, optionally substituted pyrazinyl, pyrimidinyl, pyrrolyl, imidazolyl, triazolyl, oxazolyl, thioxazolyl; and $R_1$, $R_2$, $R_3$, and $R_4$ are independently selected from the group consisting of hydrogen, $C_{1-8}$alkyl, $C_{2-8}$alkenyl, $C_{2-8}$alkynyl, $C_{3-8}$cycloalkyl, $C_{1-8}$haloalkyl, $C_{6-10}$aryl, amino-$C_{1-8}$alkyl, hydroxy-$C_{1-8}$alkyl, $C_{1-8}$alkoxy-$C_{1-8}$alkyl, and $C_{1-8}$alkanoyl, or $NR_1R_2$ taken in combination form a 3 to 7 member ring which may comprise 0, 1, or 2 additional ring heteroatoms selected from N, O, and S.

Another embodiment of the present invention relates to methods of treating ischemia-related conditions by administering to a patient in need of such treatment a compound of Formula II, or a prodrug thereof:

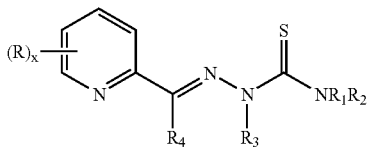

Formula II wherein
R, $R_1$, $R_2$, $R_3$, and $R_4$ are independently selected from the group consisting of hydrogen, optionally substituted alkyl, optionally substituted alkenyl, optionally substituted alkynyl, optionally substituted cycloalkyl, optionally substituted haloalkyl, optionally substituted aryl, optionally substituted aminoalkyl, optionally substituted hydroxyalkyl, optionally substituted alkoxyalkyl, and optionally substituted alkanoyl, or $NR_1R_2$ taken in combination form a 3 to 7 member ring which may comprise 0, 1, or 2 additional ring heteroatoms selected from N, O, and S; and x is an integer of 0 to 5.

And, more particularly wherein;

x is 0, 1, 2, or 3

R, $R_1$, $R_2$, $R_3$, and $R_4$ are independently selected from the group consisting of hydrogen, $C_{1-8}$alkyl, $C_{2-8}$alkenyl, $C_{2-8}$alkynyl, $C_{3-8}$cycloalkyl, $C_{1-8}$haloalkyl, $C_{6-10}$aryl, amino-$C_{1-8}$alkyl, hydroxy-$C_{1-8}$alkyl, $C_{1-8}$alkoxy-$C_{1-8}$alkyl, and $C_{1-8}$alkanoyl, or $NR_1R_2$ taken in combination form a 3 to 7 member ring which may comprise 0, 1, or 2 additional ring heteroatoms selected from N, O, and S.

Still another embodiment of the present invention relates to methods of treating ischemia-related conditions by administering to a patient in need of such treatment a compound or prodrug according to Formula III:

wherein

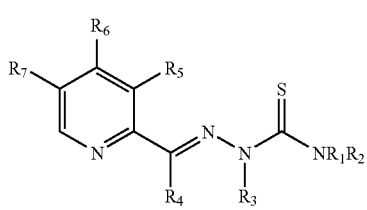

Formula III wherein:
R, $R_1$, $R_2$, $R_3$, and $R_4$ are independently selected from the group consisting of hydrogen, $C_{1-8}$alkyl, $C_{2-8}$alkenyl, $C_{2-8}$alkynyl, $C_{3-8}$cycloalkyl, $C_{1-8}$haloalkyl, $C_{6-10}$aryl, amino-$C_{1-8}$alkyl, hydroxy-$C_{1-8}$alkyl, $C_{1-8}$alkoxy-$C_{1-8}$alkyl, and $C_{1-8}$alkanoyl, or $NR_1R_2$ taken in combination form a 3 to 7 member ring which may comprise 0, 1, or 2 additional ring heteroatoms selected from N, O, and S;

$R_6$ is hydrogen, hydroxy, amino, or $C_{1-8}$alkyl;

$R_5$ and $R_7$ are independently selected from the group consisting of hydrogen, halide, hydroxy, thiol, amino, hydroxyamino, mono-$C_{1-8}$alkylamino, di($C_{1-8}$alkyl)amino, $C_{1-8}$alkoxy, $C_{1-8}$alkyl, $C_{2-8}$alkenyl, and $C_{2-8}$alkynyl.

A most preferred embodiment of the present invention relates to methods of treating ischemia-related conditions by administering to a patient in need of such treatment PAN 811 (3-aminopyridine-2-carboxaldehyde thiosemicarbazone) of the following formula:

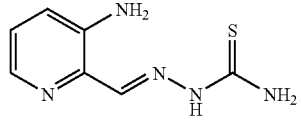

Preferred embodiments of the present invention relates to methods of treating specific ischemia-related conditions, including but not limited to Alzheimer's disease, Parkinson's disease, Coronary artery bypass graft surgery, Global cerebral ischemia due to cardiac arrest, focal cerebral infarction, cerebral hemorrhage, hemorrhage infarction, hypertensive hemorrhage. hemorrhage due to rupture of intracranial vascular abnormalities, subarachnoid hemorrhage due to rupture of intracranial arterial aneurysms, hypertensive encephalopathy, carotid stenosis or occlusion leading to cerebral ischemia, cardiogenic thromboembolism, spinal stroke and spinal cord injury, diseases of cerebral blood vessels: e.g., atherosclerosis, vasculitis, Macular degeneration, myocardial infarction, cardiac ischemia and superaventicular tachyarrhytmia.

The means for synthesis of compounds useful in the methods of the invention are well known in the art. Such synthetic schemes are described in U.S. Pat. Nos. 5,281,715; 5,767,134; 4,447,427; 5,869,676 and 5,721,259; all of which are incorporated herein by reference in their entirety.

Pharmaceutical Compositions

Another aspect of the invention pertains to pharmaceutical compositions of thiosemicarbazones useful in the methods of the invention. The pharmaceutical compositions of the invention typically comprise a compound useful in the methods of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strej an, et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., one or more thiosemicarbazones) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A compound of the invention can be formulated into a pharmaceutical composition wherein the compound is the only active agent therein. Alternatively, the pharmaceutical composition can contain additional active agents. For example, two or more compounds of the invention may be used in combination.

This invention is further illustrated by the following examples which should not be construed as limiting. The contents of all references, patents, and published patent applications cited throughout this application, as well as the figures, are incorporated herein by reference.

EXEMPLIFICATION

Example 1

Comparison of the Neuroprotective Potency of PAN-811 with Other Known Neuroprotectants 1. Objective The purpose of this study was to compare the neuroprotective capacity of PAN-811 (3-aminopyridine-2-carboxaldehyde thiosemicarbazone; $C_7H_9N_5S$; MW=195) with known neuroprotectants, such as vitamin E, lipoic acid and *ginko biloba* in a cell-based model of Alzheimer's disease-associated oxidative stress.

2. Materials and Methods 2.1. Study Design
  2.1.1. Isolation and Acculturation of Cells.
  Primary cortical neurons were isolated from a 17 day old rat embryonic brain and seeded on 96-well plate at 50,000 cells/well in regular neurobasal medium for 2-3 week. Twice, half the amount of medium was replaced with fresh neurobasal medium containing no antioxidants.
  2.1.2. Treatment with PAN-811 Other Known Neuroprotectants and $H_2O_2$
  PAN-811 was dissolved in EtOH at 1 mg/ml (~5 mM), and further diluted in medium to final concentration at 0.1 µM, 1 µM, and 10 µM. Other known neuroprotectants were dissolved in the proper solvent and diluted into final concentration as indicated. Neurons were pre-treated with PAN-811, known neuroprotectants or vehicle for 24 hours, and then subjected to oxidative stress induced by hydrogen peroxide (final concentration 150 µM). Controls include untreated cells (no compounds and hydrogen peroxide treatment), cells treated with compound only, and cells exposed to hydrogen peroxide but not compounds. Untreated cells were used as a control to evaluate both toxicity and improved viability of neurons. Each assay was performed in triplicate.

2.1.3. Evaluation of Cellular Function

After 24 hours, the cultures were evaluated for viability and mitochondrial function using a standard MTS Assay (Promega). The manufacturer's protocols were followed.

2.2. Materials

Neurobasal medium, Invitrogen
B27-AO, Invitrogen
PAN-811, Vion Pharmaceuticals, Inc.
Hydrogen peroxide, Calbiochem
EtOH, Sigma
Vitamin E, Sigma
Lipoic acid, Sigma
*Ginkgo Biloba*, CVS
MTS Assay kit, Promega 2.3. Equipment Balance, Mettler-Toledo, Inc.
Adjustable pipettes, Finnpipette
Cell culture hood, Thermo Form a
Cell culture incubator, Thermo Form a
Plate reader, Bio-Rad Model 550

3. Results 3.1. Experiment

Experiments were carried out following the procedures described in the Study Design described above. PAN-811 was dissolved in EtOH at 1 mg/ml (~5 mM), and further diluted in neurobasal medium to final concentration at 0.1 µM, 1 µM, and 10 µM. Lipoic acid was dissolved in EtOH at concentration 240 mM, and further diluted in the neurobasal medium to final concentration at 10 uM, 25 uM, 50 uM and 100 uM. Vitamin E dissolved in EtOH at concentration 100 mM, and further diluted in the neurobasal medium to final concentration at 50 uM, 100 uM, 200 uM and 400 uM. *Ginkgo Biloba* was dissolved in dH$_2$O at concentration 6 mg/ml, and further diluted in the neurobasal medium to final concentration at 2.5 ug/ml, 5 ug/ml, 25 ug/ml, 250 ug/ml. At the end of the treatment, the medium was replaced with 100 µl fresh pre-warmed neurobasal medium plus B27 (-AO). The plates were returned to the incubator at 37° C. with 5% CO$_2$ for one hour. Subsequently 20 µl MTS reagent was added to each well and plates were incubated at 37° C. with 5% CO$_2$ for an additional two hours. The absorbance at 490 nm for each well was recorded with the BioRad plate reader (Model 550). Wells containing medium alone were used as blanks. Each data point is the average of three separate assay wells. Untreated cells were used as a control to calculate the cell viability and neuroprotective capacity. Two weeks old primary cultures were used for this set of study. Please see FIG. 1 for results.

Conclusions

PAN-811 displayed good neuroprotective capacity at concentrations from 1-10 µM, even under harsh H$_2$O$_2$ treatment. Vitamin E and Lipoic acid displayed minimal neuroprotective capacity under harsh treatment. *Ginkgo Biloba* displayed a certain level of neuroprotection under harsh treatment.

PAN-811 displayed significant neuroprotection at 1-10 µM final concentration, even under harsh H$_2$O$_2$ treatment. The neuroprotective efficacy of PAN-811 significantly exceeded that of the other known neuroprotectants; Vitamin E, lipoic acid, and *Ginkgo Biloba*.

Example 2

The Effect of PAN-811 on Reactive Oxygen Species (ROS) Generation in Neuronal Cells Objective The purpose of this study was to assess the capability of PAN-811 to reduce ROS generation in a cell-based model of Alzheimer's disease-associated oxidative stress.

1. Materials and Methods 1.1 Study Design 1.1.1 Isolation and Acculturation of Cells.

Primary cortical neurons were isolated from a 17 day old rat embryonic brain and seeded in 96-well plates at 50,000 cells/well in regular neurobasal medium for 2-3 weeks. Twice, half the amount of medium was replaced with fresh neurobasal medium without antioxidants.

1.1.2 Pre-loading of Cells with CM-H$_2$DCFDA Dye and Treatment with PAN-811 and H$_2$O$_2$ Primary cortical neurons were rinsed once with HBSS buffer and incubated with 10 µM 5-(and-6)-chloromethyl-2', 7'-dichlorodihydrofluorescein diacetate, acetyl ester (CM-H$_2$DCFDA) to pre-load the dye. The cells were then rinsed with HBSS buffer once and treated with PAN-811 at final concentration at 0.1, 1, 5, and 10 µM for 1 hour, and further subjected to oxidative stress induced by hydrogen peroxide at 300 µM for 2 hours.

1.1.3. Evaluation of ROS Generation in Neuronal Cells c-DCF fluorescence at 485/520 nm (Ex/Em) for each well was recorded with the BMG polar star plate reader and used to evaluate ROS generation in cells. Untreated cells loaded with the dye were used as controls to calculate the c-DCF fluorescence change. Each assay was performed in triplicate.

1.2 Materials

Neurobasal medium, Invitrogen
B27-AO, Invitrogen
HBSS buffer, Invitrogen
CM-H$_2$DCFDA, Molecular Probes
PAN-811, Vion Pharmaceuticals, Inc.
Hydrogen peroxide, Calibiochem
EtOH, Sigma
PEG-300, Sigma 1.3 Equipment Balance, Mettler-Toledo, Inc.
Adjustable pipettes, Finnpipette
Cell culture hood, Thermo Form a
Cell culture incubator, Thermo Form a
Polarstar Fluorescence plate reader, BMG 2.0 Results 2.1 Experiment Experiments were carried out following the procedures described in the Study Design described above. The c-DCF fluorescence at 485/520 nm (Ex/Em) for each well was recorded with the BMG polar star plate reader. Wells containing cells without dye were used as blanks. Each data point is the average of three separate assay wells. Untreated cells loaded with the dye were used as a control to calculate the c-DCF fluorescence change. Two weeks old primary cultures were used for the study.

3.0 Discussion

CM-H$_2$DCFDA is a cell-permeant indicator for ROS that is nonfluorescent until the acetate groups are removed by intracellular esterases and oxidation occurs within the cell. It has been widely employed to detect the generation of reactive oxygen species (ROS) in cells and animals. Here it has been used as a tool to assess the effect of PAN-811 on ROS generation in neuronal cells following the procedures described in the study design. As FIG. 2 illustrates, PAN-811 displayed good capacity to reduce H$_2$O$_2$-induced ROS generation, as well as basal level ROS generation in neuronal cells. The parallel control experiment using buffer, PGE-300/EtOH, instead of PAN-811 showed no effect on ROS generation in cells. Experiments were repeated four times in different batch of cells and similar results were obtained. See FIG. 2 for a representative experiment.

4.0 Conclusions

PAN-811 significantly reduced both H$_2$O$_2$-induced ROS generation (~30% at 10 μM) and the basal level of ROS generation (~50% at 10 μM) in primary neuronal cells.

Literahure (1). Gibson G E, Zhang H, Xu H, Park L C, Jeitner T M. (2001). Oxidative stress increases internal calcium stores and reduces a key mitochondrial enzyme. Biochim Biophys Acta. March 16; 1586(2):177-89.
(2). Chignell C F, Sik R H. (2003). A photochemical study of cells loaded with 2',7'-dichlorofluorescin: implications for the detection of reactive oxygen species generated during UVA irradiation. Free Radic Biol Med. April 15; 34(8): 1029-34.

Example 3

PAN-811, a Potential Neuroprotectant for Hypoxia- or Hypoxia/Hypoglycemia-Induced Neurotoxicity

1.0 Introduction

Reducing neuronal damage in the first minutes after a stroke is an important strategy to gain effective therapy. During stroke, the transport of oxygen and glucose to localized regions of the brain is halted by thrombo-embolic blockage of an artery, which causes neuronal loss in the central core of an infarction. The cells in the central core die very quickly via a necrotic mechanism. The area of the brain surrounding an ischemic infarct that retains its structure but is functionally (electrically) silent is termed the penumbra. The penumbra is a temporal zone, in that its evolution toward infarction is a relatively progressive phenomenon (Touzani et al., 2001). This zone provides the possibility of salvaging some of the brain function and the therapeutic window for treatment of the penumbra is much longer than that for the infarcted area. The penumbra can also be described as a region of constrained blood supply in which energy metabolism is preserved. Therefore the penumbra is the target of neuroprotective therapy as well as for agents such as hyperbaric oxygen that would reactivate the dormant neurons. As such, immediate damage from injury in CNS trauma may not be reversible but the progression of the chain of events that aggravate brain damage, predominantly global cerebral hypoxia/ischemia, could be prevented by an effective strategy for neuroprotection. For example, administration of a neuroprotectant before and during coronary artery bypass graft (CABG) operation could efficiently prevent the neurodegeneration caused by the short term changes in blood flow to the brain (leading to a mild hypoxic/hypoglycemic state) during surgery. Thus compounds capable of both significant neuroprotection as well as rescue of neurons after they have received damage are of great interest.

2.0 Objective

The purpose of this study was to understand whether PAN-811 is able to protect hypoxia- or hypoxia/hypoglycemia (H/H)-induced neurotoxicity in vitro. PAN-811 has already been shown in related work to apply significant neuroprotection to primary neurons treated with H$_2$O$_2$.

3.0 Materials and Methods 3.1 Materials
  Neurobasal medium, Invitrogen
  B27-AO, Invitrogen
  PAN-811, Vion Pharmaceuticals
  EtOH, Sigma
  DMSO, Sigma
  PEG-300, Sigma
  MTS Assay kit, Promega
  LDH Assay kit, Sigma 3.2. Equipment
  Balance, Mettler-Toledo, Inc.
  Adjustable pipettes, Finnpipette
  Cell culture hood, Thermo Form a
  Cell culture incubator, Thermo Form a
  Plate reader, Bio-Rad Model 550
  FYRITE Gas Analyzer, Bacharach, Inc
  Modular Incubator Chamber-101TM, Billups-Rothenberg, Inc.

3.3. Abbreviations:
  BSS=Balanced salt solution
  CABG=Coronary artery bypass graft
  d.i.v.=Days in vitro
  EtOH=Ethanol
  H/H=Hypoxia/hypoglycemia
  LDH=Lactate dehydrogenase
  MCAO=Middle cerebral artery occlusion
  NB=Neurobasal medium
  NMDA=N-methyl-D-aspartate
  PEG=Polyethylene glycol 3.4 Study Design
  3.4.1 Neuronal Culture
  Experiments were performed in a 96-well plate format. Cortical neurons were seeded at a density of 50,000 cells/well on poly-D-lysine coated surface, and cultured in serum-free medium (NB plus B27 supplement) to obtain cultures high-enriched for neurons. Neurons were cultured for over 14 d.i.v. to increase cell susceptibility to excitatory amino acids (Jiang et al., 2001). Six replicate wells were treated as a group to facilitate assay quantitation.

3.4.2 Induction of Neurotoxicity—in vitro Models

As shown in the table below, glucose concentration normally is over 2.2 mM in the brain. It goes down to 0.2 mM and 1.4 mM in the central core and penumbra respectively during ischemia. Glucose levels return to normal 1 or 2 hours after recirculation (Folbergrová et al., 1995).

TABLE 1

| | Glucose Concentrations (mmol/kg) | | |
|---|---|---|---|
| | Sham | 2-hour MCAO | 1-hour recirculation |
| Focus | 2.12 ± 0.18 | 0.21 ± 0.09 | 2.65 ± 0.19 |
| Penumbra | 2.20 ± 0.16 | 1.42 ± 0.34 | 2.69 ± 0.17 |

To understand the effect of glucose concentration on hypoxia-induced neurotoxicity, we have tested different doses of glucose. As shown in FIG. 3, reduction of the glucose concentration to 2.9 mM did not result in neuronal cell death by comparison to normal conditions where the glucose concentration is 25 mM. When glucose concentration went down to 0.4 mM, robust cell death occurred as indicated by the MTS assay.

To mimic the cerebral environments of a stroke, we established 3 in vitro model systems. The extreme H/H model (0.4 mM glucose) is a mimic of the environment in the central core of an infarct; the mild H/H model (1.63 mM glucose) is a mimic of the environment in the penumbra during MCAO; and the hypoxia only model (neurons in normal in vitro glucose concentration—25 mM) is a mimic of the environment in the penumbra after reperfusion since the possible cell death after reperfusion is predominantly a result of the hypoxic effect rather then energy failure.

Hypoxia/hypoglycemia was obtained by reducing glucose concentration down to 0.4 mM and 1.63 mM for extreme H/H and mild H/H respectively. BSS (116.0 mM NaCl, 5.4 mM KCl, 0.8 mM $MgSO_4 \cdot 7H_2O$, 1.0 mM $NaH_2PO_4$, 1.8 mM $CaCl_2 \cdot 2H_2O$, 26.2 mM $NaHCO_3$, and 0.01 mM Glycine) or BSS with 25 mM glucose were de-gassed for 5 minutes prior to use. Culture medium in the plates for hypoxia was replaced with BSS or BSS with glucose. Meanwhile, culture medium in the plates for normoxia was replaced with non de-gassed BSS or BSS with glucose. Cells were committed to hypoxic conditions by transferring the plates into a sealed container (Modular Incubator Chamber-101TM, Billups-Rothenberg, Inc.), applying a vacuum for 20 minutes to remove O2 or other gases from the culture medium, and then refilling the chamber with 5% CO2 and 95% N2 at a pressure of 30 psi for 1 minute. The level of O2 in the chamber was determined to be zero with an $O_2$ indicator (FYRITE Gas Analyzer, Bacharach, Inc.). Culture plates were maintained in the chamber for 6 hours. As an experimental control, duplicate culture plates were maintained under normal culture condition (5% CO2 and 95% ambient air) for the same duration. After a 6-hour treatment plates were removed from the chamber and the medium in both the hypoxic and normoxic cultures was replaced with a termination solution (DMEM supplemented with 1× sodium pyruvate, 10.0 mM HEPES, and 1×N2 supplement) containing 25 mM glucose and cultured in 5% CO2 and 95% ambient air conditions. Neurons were treated with varying concentrations of PAN-811 or vehicle as a negative control. MK801 was utilized as a positive control. Mitochondrial function and cell death were evaluated at 24 or 48 hours post H/H insult with the MTS and LDH analyses (see below).

In the sole hypoxia model, the neurons were pre-treated with solvent or PAN-811 for 24 or 48 hours. Treatment with drug was continued during and subsequent to a 24-hour period of hypoxia. Cellular morphology and function (MTS and LDH assays) were measured 24 or 48 hours subsequent to the hypoxic insult.

3.4.3 Morphology Monitoring

Figure 4:
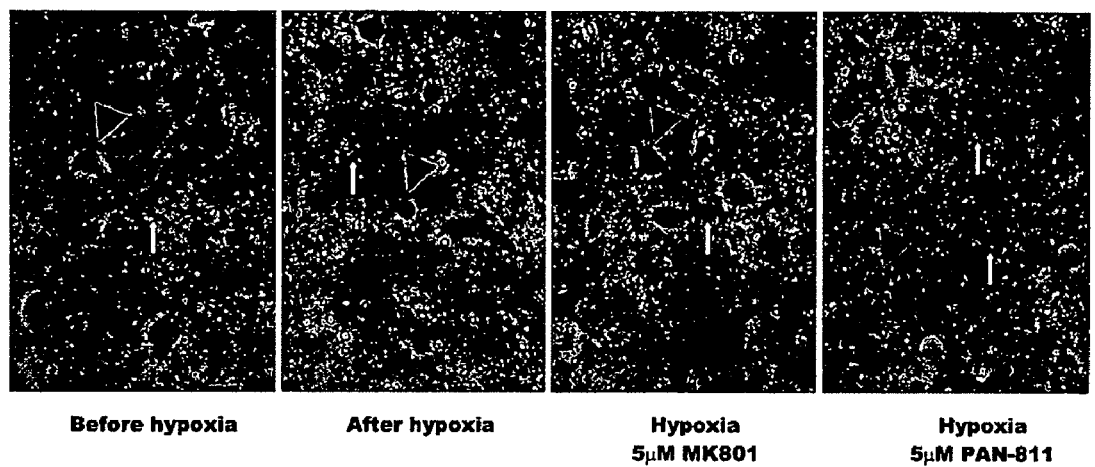
FIG. 4 are representative histological photographs of cells under hypoxic conditions with and without neuroprotectants, MK801 and PAN-811.

Neuronal cell death evaluated morphologically as seen in FIG. 4. Neurons prior to hypoxia are healthy with phase-brilliant cell soma (arrow head) and intact neuronal processes (open arrow). The processes and their branches form a dense network in the background. Hypoxia causes shrinkage of the cell body and collapse of the neuronal processes and network. PAN-811, as well as the glutamate NMDA receptor antagonist MK801 at doses of 5 µM show efficient protection from neuronal cell death and partially reservation of the neuronal processes.

3.4.4 MTS Assay

The MTS assay is a colorimetric assay that measures the mitochondrial function in metabolically active cells. This measurement indirectly reflects cell viability. The MTS tetrazolium compound is reduced in metabolically active mitochondria into a colored formazan product that is soluble in tissue culture medium, and can be detected via its absorbance 490 nm. 20 µl of MTS reagent (Promega) are added to each well of the 96 well assay plates containing the samples in 100 µl of culture medium. The plate is then incubated in a humidified, 5% $CO_2$ atmosphere at 37° C. for 1-2 hours until the color is fully developed. The absorbance at 490 nm was recorded using a Bio-Rad 96 well plate reader.

3.4.5 LDH Assay

Lactate dehydrogenase (LDH) assay is based on the reduction of NAD by the action of LDH. The resulting reduced NAD (NADH) is utilized in the stoichiometric conversion of a tetrazolium dye. If cell-free aliquots of medium from cultures given different treatments are assayed, then the amount of LDH activity can be used as an indicator of relative cell death as well as a function of membrane integrity. A 50 µl aliquot of culture medium from a well in tested 96-well plate is transferred into a well in unused plate and supplemented with 25 µl of equally-mixed Substrate, Enzyme and Dye Solutions (Sigma). The preparation is incubated at room temperature for 20-30 minutes, and then measured spectrophotometrically at wavelength of 490 nm.

4. RESULTS

4.1 Sole Hypoxia Model

4.1.1. Efficacy and Toxicity of PAN-811

Figure 5:
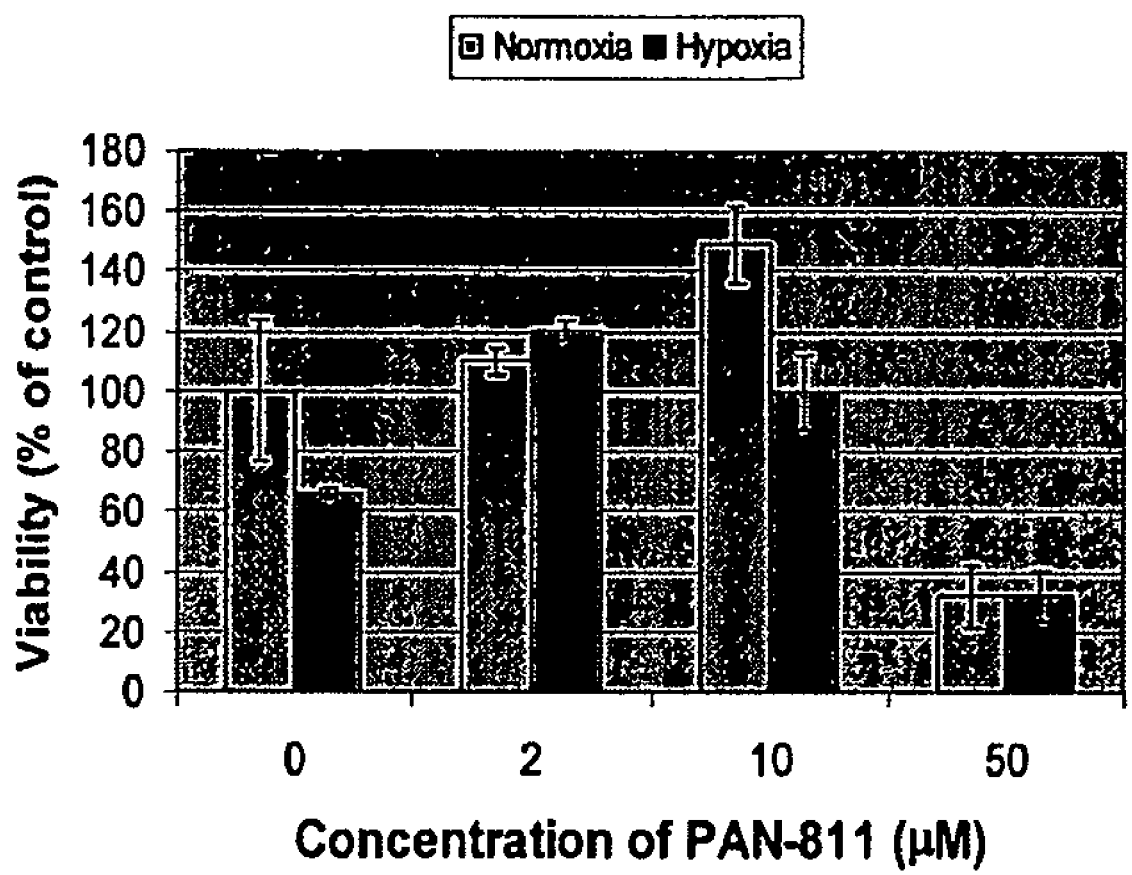
FIG. 5 is a graphic representation of the neuroprotective effects of PAN-811 under normoxic and hypoxic conditions.

Cortical neurons were treated with PAN-811 for 48-hour prior to hypoxia; PAN-811 remained present during 24-hour hypoxia and for a 48-hour period subsequent to hypoxia. PAN-811 at dose of 2 µM completely blocked the cell death but 50 µM was toxic (see FIG. 5).

4.1.2. Comparison to Other Neuroprotectants

Cortical neurons were treated with 2 µM PAN-811, 1:80 green tea or 5 µM MK801 for 24 hours prior to, during and subsequent to a 24-hour period of hypoxia. PAN-811 demonstrated highest efficacy among reagents tested, completely blocking neuronal cell death and mitochondrial dysfunction.

Mild H/H Model

4.1.3. PAN-811 Protected Neurons from Mild H/H-induced Neurotoxicity Before and During Insult.

Embryonic (E17) rat cortical neurons were cultured for 15 days, treated with PAN-811 and vehicle 24-hours before and during hypoxia/hypoglycemia (6-hours). MTS and LDH assays were carried out 17 hours post to the insults. PAN-811 at 5 μM, but not a 1:1,520 dilution of PEG:EtOH (which corresponds to the mount of vehicle in 5 μM PAN-811), completely protected hypoxia/hypoglycemia-induced mitochondria dysfunction and neuronal cell death.

Figure 6:
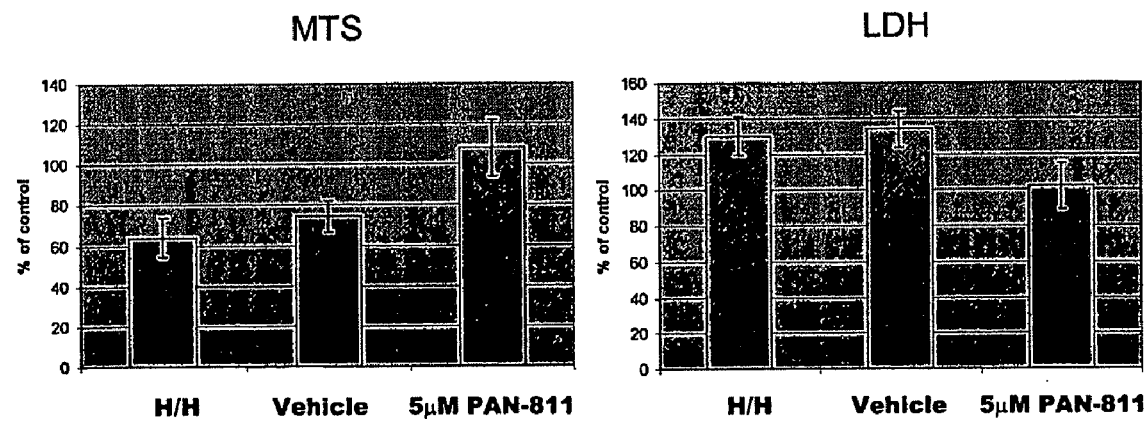
FIG. 6 are graphic representations of the toxicity of PAN-811, under hypoxic/hypoglycemic conditions.

The data shown in FIG. 6 are representative. A summary of 6 experiments that cover a concentration range of 2-50 μM is shown in the following Table 2.

| Date | Culture age (days) | Pre-treatment (hours) | H/H duration (hours) | Post to H/H (hours) | Comments |
|---|---|---|---|---|---|
| Apr. 17, 2003 | 13 | 24 | 6 | 48 | 2 μM: 100% protected |
| May 2, 2003 | 22 | 24 | 6 | 24 | 2 μM: 100% protected |
| May 8, 2003 | 42 | 24 | 6 | 24 | 2 μM: 100% protected |
| Jul. 9, 2003 | 13 | 24 | 6 | 20 | 2 μM: 100% protected |
| Jul. 13, 2003 | 15 | 24 | 6 | 24 | 10 μM: 100% protected |
| Jul. 25, 2003 | 15 | 24 | 6 | 24 | 5 μM: 100% protected |

** Test range started from 5 μM for the experiments of Jul. 13, 2003 and Jul. 25, 2003

4.2.2. PAN-811 Protected Cells from Mild H/H-induced Neurotoxicity During and Especially after the Insults.

Figure 7:
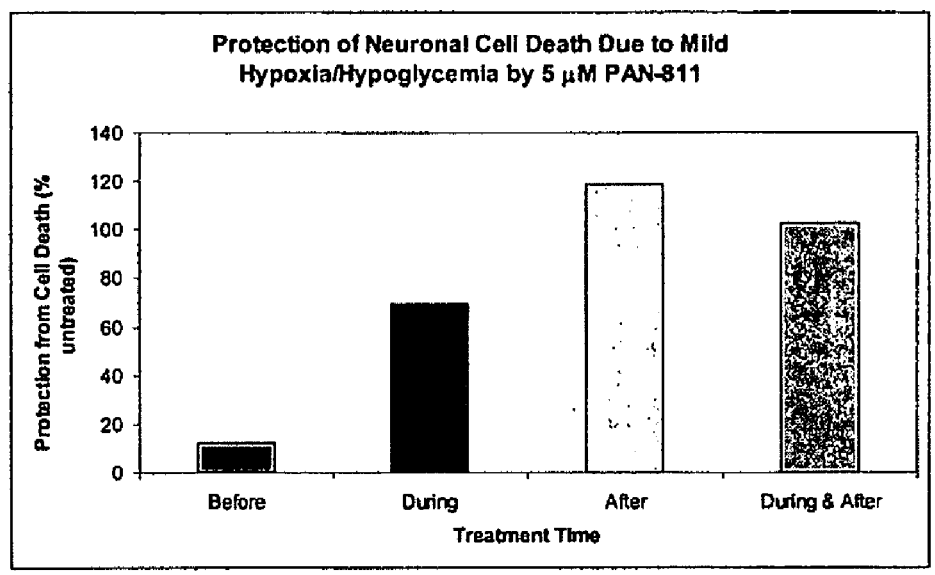
FIG. 7 is a graphic representations of the protective effects of PAN-811 on neuronal cell death due to mild hypoxic/hypoglycemic conditions.

The neurons were cultured for 15 days, and treated with PAN-811 or PEG:EtOH (7:3) as vehicle for a 24-hour period prior to 6-hour H/H (Before Group). Alternatively the neurons were cultured for 16 days, and then treated with above reagents during 6-hour H/H (During Group), treated for a 6-hour H/H period and 48-hour period subsequent to the H/H (During and After Group), or treated for a 48-hour period subsequent to the H/H (After group). The LDH assay was carried out 48 hours after the period of H/H. The results demonstrated that PAN-811 protected neuronal cell death when treating the neurons during and especially after H/H, but marginally before H/H, see FIG. 7.

4.2. Extreme H/H Model

PAN-811 at ≦50 μM did not protect neuronal cell death (data not shown).

5. Conclusions 5.1. PAN-811 at 2 μM completely protected sole hypoxia- and mild H/H induced neurotoxicity. PAN-811 at 100 μM only partially blocked extreme H/H-induced neuronal cell death so PAN-811 is unlikely to be involved in energy metablism.

5.2. PAN-811 significantly protects neurons from cell death when administered either during or subsequent to a hypoxic or ischemic insult.

5.3. The efficacy of PAN-811 is significantly greater than that of MK801 and/or green tea.

5.4. PAN-811 at 50 μM is toxic to neurons in long-term exposure (120-hour exposure).

6. References

1. Jiang, Z.-G., Piggee, C. A., Heyes, M. P., Murphy, C. M., Quearry, B., Zheng, J., Gendelman, H. E., and Markey, S. P. Glutamate is a principal mediator of HIV-1-infected immune competent human macrophage neurotoxicity. J. Neuroimmunology 117(1 2):97-107, 2001.

2. Folbergrová, J., Zhao, Q., Katsura, K., and Siesjö, B. K. N-tert-butyl-phenylnitrone improves recovery of brain energy state in rats following transient focal ischemia. Proc. Natl. Acad. Sci. USA 92:5057-5061, 1995.

3. Touzani, O., Roussel, S., and MacKenzie, E. T. The ischemic penumbra. Curr. Opin. Neurol. 14:83-8, 2001.

Example 4

PAN-811 Displays Significant Neuroprotection in an In Vivo Model of Transient Focal Brain Ischemia

1. Introduction

Reducing neuronal damage in the first minutes after a stroke is an important strategy to gain effective therapy. During stroke, the transport of oxygen and glucose to localized regions of the brain is halted by thrombo-embolic blockage of an artery, which causes neuronal loss in the central core of an infarction. The cells in the central core die very quickly via a necrotic mechanism. The area of the brain surrounding an ischemic infarct that retains its structure but is functionally (electrically) silent is termed the penumbra. The penumbra is a temporal zone, in that its evolution toward infarction is a relatively progressive phenomenon (Touzani et al., 2001). This zone provides the possibility of salvaging some of the brain function and the therapeutic window for treatment of the penumbra is much longer than that for the infarcted area. The penumbra can also be described as a region of constrained blood supply in which energy metabolism is preserved. Therefore the penumbra is the target of neuroprotective therapy as well as for agents such as hyperbaric oxygen that would reactivate the dormant neurons. As such, immediate damage from injury in CNS trauma may not be reversible but the progression of the chain of events that aggravate brain damage, predominantly global cerebral hypoxia/ischemia, could be prevented by an effective strategy for neuroprotection. For example, administration of a neuroprotectant before and during coronary artery bypass graft (CABG) operation could efficiently prevent the neurodegeneration caused by the short term changes in blood flow to the brain (leading to a mild hypoxic/hypoglycemic state) during surgery. Thus compounds capable of both significant neuroprotection as well as rescue of neurons after they have received damage are of great interest.

2. Objective

PAN-811 has shown significant neuroprotection in in vitro models of oxidative stress and ischemia. This prior work coupled with the known toxicity profile and pharmokinetic data on the compound are highly suggestive of its potential us in the treatment of stroke.

3. Materials and Methods 3.1 Materials
PAN-811, Vion Pharmaceuticals
EtOH, Sigma
PEG-300, Sigma
MTS Assay kit, Sigma 3.2. Abbreviations:
CABG=Coronary artery bypass graft
EtOH=Ethanol
H/H=Hypoxia/hypoglycemia
MCAO=Middle cerebral artery occlusion
PEG=Polyethylene glycol

3.3 Study Design 3.3.1 In vitro studies. Prior to embarking on in vivo studies PAN-811 was tested in several cellular models of neurodegeneration.

3.3.1.1. Neuronal culture. Enriched neuronal cultures were prepared from 15-day-old Sprague-Dawley rat embryos. Using aseptic techniques, the rat embryos were removed from the uterus and placed in sterile neuronal culture medium. Using a dissecting microscope, the brain tissue was removed from each embryo, with care taken to discard the meninges and blood vessels. The cerebellum was separated by gross dissection under the microscope, and only cerebellar tissue was used for the culture. Cells were dissociated by trituration of the tissue and were plated at a density of $5 \times 10^5$ cells/well onto 48-well culture plates precoated with poly(L-lysine). Cultures were maintained in a medium containing equal parts of Eagle's basal medium (without glutamine) and Ham's F-12k medium supplemented with 10% heat-inactivated horse serum, 10% fetal bovine serum, 600 µg/ml glucose, 100 µg/ml glutamine, 50 U/ml penicillin, and 50 µg/ml streptomycin. After 48 h, 10 µM cytosine arabinoside was added to inhibit non-neuronal cell division. Cells were used in experiments after 7 days in culture.

3.3.1.2 Neurotoxicity of PAN-811. Cells were treated with varying amounts of PAN-811 (0-100 µM) for 24 hrs. Cell viability was determined in the MTT assay.

3.1.3.3 Induction of neurotoxicity—in vitro models. Four in vitro models of excitotoxicity were studied. Cells were either exposed to H/H conditions for 3 hrs or treated for 45 min with either glutamate (100 µM), staurosporine (1 µM) or veratridine (10 µM). All cells were cotreated with or without PAN-811 (10 µM) in Locke's solution. At the conclusion of the respective excitotoxic exposures, the condition medium (original) was replaced. H/H was induced by incubating the cells in a humidified airtight chamber saturated with 95% nitrogen, 5% $CO_2$ gas for 3 hrs. in Locke's solution without added glucose.

3.1.3.4 MTT Assay. 24 hrs. after the excitotoxic insult cell viability assessments were made. Cell damage was quantitatively assessed using a tetrazolium salt colorimetric assay with 3-(4,5-dimethylthiazol-2-yl)-2,5-diphenyltetrazolium (MTT; Sigma Chemical Co., St. Louis, Mo.). Briefly, the dye was added to each well (final concentration, 1.5 mg/ml), cells were incubated with MTT-acidified isopropanol (0.1 N HCl in isopropanol), and the absorbance intensity (540 nm) of each sample was measured in a 96-well plate reader. Values are expressed relative to vehicle-treated control cells that were maintained on each plate, and the percentage change in cell viability was calculated.

3.1.2 In vivo Studies.

3.1.2.1 MCAO. 36 male Sprague-Dawley rats (270-330 g; Charles River Labs, Raleigh, Va.) were used in this study. Anesthesia was induced by 5% halothane and maintained at 2% halothane delivered in oxygen. Body temperature was maintained normothermic ($37 \pm 1°$ C.) throughout all surgical procedures by means of a homeothermic heating system (Harvard Apparatus, South Natick, Mass.). Food and water were provided ad libitum before and after surgery, and the animals were individually housed under a 12-h light/dark cycle. Rats were anesthetized and prepared for temporary focal ischemia using the filament method of middle cerebral artery occlusion (MCAO) and reperfusion. Briefly, the right external carotid artery was isolated and its branches were coagulated. A 3-0 uncoated monofilament nylon suture with a rounded tip was introduced into the internal carotid artery via the external carotid artery and advanced (approximately 22 mm from the carotid bifurcation) until a slight resistance was observed, thus occluding the origin of the MCA. The endovascular suture remained in place for 2 h and then was retracted to allow reperfusion of blood to the MCA. After MCAO surgery, animals were placed in recovery cages with ambient temperature maintained at 22° C. During the 2-h ischemia period and the initial 6-h postischemia period, 75-W warming lamps were also positioned directly over the top of each cage to maintain body temperature normothermic throughout the experiment.

3.1.2.2 Treatment with PAN-811. Rats were treated 10 minutes prior to MCAO with 1/mg/kg PAN-811 via IV injection. PAN-811 was prepared as a stock solution in 70% PEG300, 30% EtOH. This stock was diluted 5-fold in sterile saline prior to injection (final concentration 1 mg/ml).

3.1.2.3 Measurement of infarct volume. For each rat brain, analysis of ischemic cerebral damage was measured as a function of total infarct volume. This was achieved using 2,3,5-triphenyl tetrazolium chloride (TTC) staining from seven coronal sections (2-mm thick). Brain sections were taken from the region beginning 1 mm from the frontal pole and ending just rostral to the corticocerebellar junction. Computer-assisted image analysis was used to calculate infarct volumes. Briefly, the posterior surface of each TTC-stained forebrain section was digitally imaged (Loats Associates, Westminster, Md.) and quantified for areas (in square millimeters) of ischemic damage.

4. Results

Figure 8:
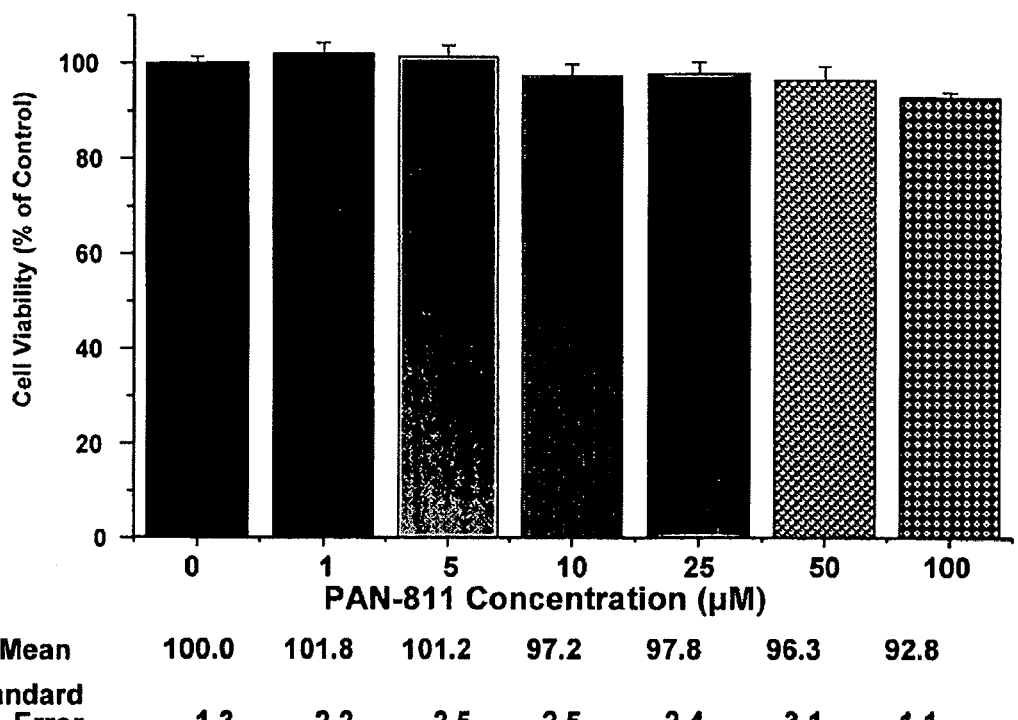
FIG. 8 is a graphic representation of the neurotoxicity of PAN-811 where cortical neurons were treated with PAN-811 for 24 hours.

4.1 In vitro Studies 4.1.1 Neurotoxicity of PAN-811. Results are presented in FIG. 1. Essentially, PAN-811 showed only slight toxicity at concentrations up to 100 µM. Maximumal toxicity was only 7.8% at the highest concentration tested (see FIG. 8).

Figure 9:
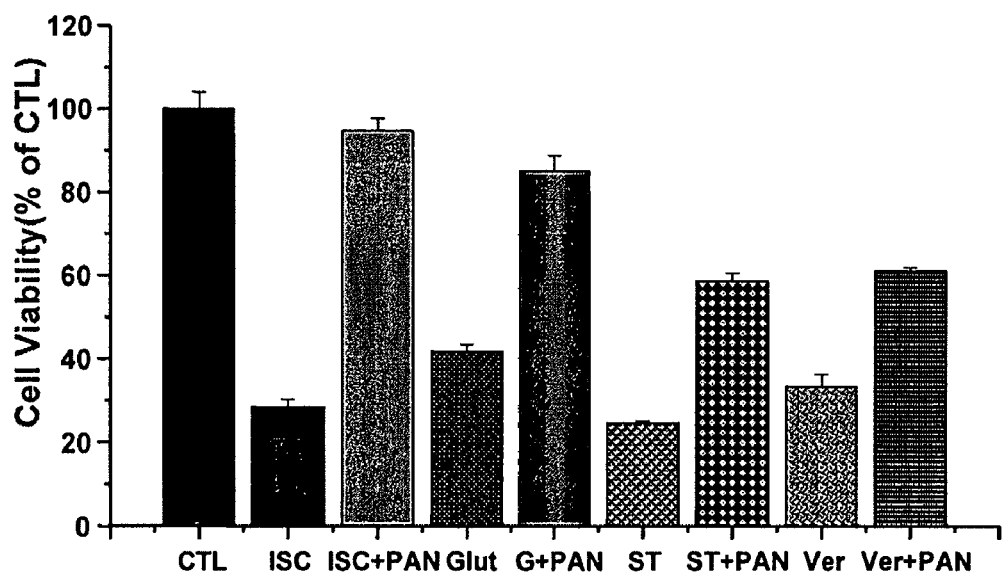
FIG. 9 is a graphic representation of the protective effects of PAN-811 against toxicity due to ischemia.

4.1.2 Neuroprotection due to PAN-811. PAN-811 was found to significantly protect neurons from for different excitotoxic insults (FIG. 2). Pre-treatment of neurons with 10 µM PAN-811 protected cells from the damage induced by a 3 hour period of hypoxia/hypoglycemia (92% protection), from 100 µM glutamate (~75%), 1 µM staurosporine, an inhibitor of protein kinase C and inducer of apoptosis (~47%) and 10 µM veratridine a sodium channel blocker (~39%). See FIG. 9.

4.2 In vivo Studies.

Results of this experiment are presented in Table 3. In total 36 rats were used for the experiment, however 11 rats were excluded due to the following reasons: 4 rats died of severe stroke without complications of hemorrhage, 4 rats were excluded due to sub acute hemorrhage (3 of them died <24 h), 1 rat was excluded due to a fire drill during surgery, 1 rat was excluded due to being statistical outlier, and 1 rat died of overdose of halothane. Of the 7 rats that died (4 from severe strokes without SAH, and 3 with SAH), 6 were untreated (vehicle) rats and only 1 was treated with PAN-811. Vehicle treated rats had a mean infarct volume of 292.96 $mm^3$ with a range from 198.75-355.81. PAN-811 treated rats had a mean infarct volume of 225.85 $mm^3$ with a range 42.36-387.08. This represents a neuroprotection of 23% ($p<0.05$). For reasons yet to be determined, more severe injury was noted in the control group than is normally measured. Accordingly, the infarct size for the PAN-811 treated animals is also larger than expected for significant neuroprotection. Despite this issue the variability in both treatment groups was excellent (10% or less of the SEM) and was as good, if not better, than most of our previously published studies.

5. Conclusions 11.1 PAN-811 is well tolerated and relatively non-toxic in both the in vitro and in vivo model systems.

11.2 Pre-treated of neurons with 10 μM PAN-811 gave significant protection against for excitotoxic insults that result in neurodegeneration.

11.3 Pre-treatment of rats 10 minutes prior to a period of transient focal brain ischemia with a single dose of PAN-811 (1 mg/kg) yielded a 23% reduction in average infarct volume.

6. References

6.1 Literature 6.1.1. Williams A J, Dave J R, Phillips J B, Lin Y, McCabe R T, and Tortella F C. (2000) Neuroprotective efficacy and therapeutic window of the high-affinity N-methyl-D-aspartate antagonist conantokin-G: in vitro (primary cerebellar neurons) and in vivo (rat model of transient focal brain ischemia) studies. *J Pharmacol Exp Ther. July;* 294(1):378-86.

7.

TABLE 3

| Vehicle Treated | | PAN-811 | |
|---|---|---|---|
| Rat # | Infarct Volume | Rat # | Infarct Volume |
| R28 | 198.75 | R21 | 42.36 |
| R17 | 208.03 | R1 | 126.42 |
| R2 | 267.38 | R30 | 143.74 |
| R11 | 270.89 | R24 | 158.83 |
| R34 | 282.51 | R3 | 196.18 |
| R19 | 308.19 | R26 | 200.08 |
| R27 | 308.45 | R23 | 218.54 |
| R36 | 334.81 | R20 | 221.46 |
| R10 | 339.85 | R25 | 224.32 |
| R4 | 347.89 | R31 | 255.36 |
| R32 | 355.81 | R5 | 267.40 |
| | | R13 | 344.47 |
| | | R16 | 375.59 |
| | | R8 | 387.08 |
| Mean | 292.96 | Mean | 225.85 |
| SD | 53.60 | SD | 96.67 |
| SEM | 16.16 | SEM | 25.84 |
| N | 11 | n | 14 |
| p value | | | 0.05 |
| % protection | | | 23% |

Table I: Infarct Volume in $mm^3$ of vehicle and PAN-811 treated rats. Rats were treated with 1 mg/kg PAN-811 10 minutes prior to MCAO. Infarct volume was determined 24 hours after surgery.

Example 5

Protection of Neurons from $H_2O_2$-induced Oxidative Stress by PAN-811

1.0 Objective

The purpose of this study was to assess the efficacy of PAN-811 as a neuroprotectant in a cell-based model of Alzheimer's disease-associated oxidative stress. Neuroprotection and cellular toxicity are determined. Various solvents were tested to determine their appropriateness as vehicles for the delivery of PAN-811.

2. Materials and Methods

2.1 Materials
Neurobasal medium, Invitrogen
B27-AO, Invitrogen
PAN-811, Vion Pharmaceuticals
Hydrogen peroxide, Calibiochem
EtOH, Sigma
DMSO, Sigma
PEG-300, Sigma
MTS Assay kit, Promega

2.2 Equipment
Balance, Mettler-Toledo, Inc.
Adjustable pipettes, Finnpipette
Cell culture hood, Thermo Form a
Cell culture incubator, Thermo Form a
Plate reader, Bio-Rad Model 550

2.3 Study Design

2.3.1 Isolation and Acculturation of Cells.

Primary cortical neurons were isolated from a 17 day old rat embryonic brain and seeded on 96-well plate at 50,000 cells/well in regular neurobasal medium for 2-3 week. Twice, half amount of medium was replaced with fresh neurobasal medium containing no antioxidants.

2.3.2 Treatment with PAN-811 & $H_2O_2$.

PAN-811 was dissolved in either EtOH or DMSO at 1 mg/ml (~5 mM), in PEG-300/EtOH (70%/30%) at 5 mg/ml (~25 mM), and further diluted in medium to final concentration at 1 μM, 5 μM, 20 μM and 50 μM. Neurons were pre-treated with PAN-811 or vehicle for 24 hours, and then subjected to oxidative stress induced by hydrogen peroxide (final concentration 60-70 μM). Controls include untreated cells (no PAN-811 and hydrogen peroxide treatment), cells treated with PAN-811 only, and cells exposed to hydrogen peroxide but not PAN-811. Untreated cells were used as a control to evaluate both toxicity and improved viability of neurons. Each assay was performed in triplicate. Equal volume of solvents (EtOH, DMSO, and PEG-300/EtOH) was added to cells to test the solvent effects on the assay.

2.3.3. Evaluation of Cellular Function

After 24 hours, the cultures were evaluated for viability and mitochondrial function using a standard MTS Assay (Promega). The manufacturer's protocols were followed.

3. Results

3.1 Experiment 1

Experiments were carried out following the procedures described in the study design. At the end of the treatment, all treatments and medium were replaced with 100 μl fresh pre-warmed neurobasal medium plus B27 (-AO). The plates were put back into the incubator at 37° C. with 5% $CO_2$ for one hour, then 20 μl MTS reagent was added to each well and plates were incubated at 37° C. with 5% $CO_2$ for an additional two hours. The absorbance at 490 nm for each well was recorded with the BioRad plate reader (Model 550). Wells containing medium alone well was used as blanks. Each data point is the average of three separate assay wells. Untreated cells were used as a control to calculate the cell viability and neuroprotective capacity. Three weeks old primary cultures were used for this set of study. Please see FIG. 10 for results.

3.2 Experiment 2

Experiments were carried out following the same procedures as experiment 1.

Two weeks old primary cultures were used for this study. Please see FIG. 11 for results.

4. Discussion

All three solvents showed minimal effects on the assay system at dilutions corresponding to final PAN-811 concentrations from 1-10 μM. DMSO displayed a certain level of neuroprotection at dilutions corresponding to final PAN-811 concentrations at or above 20 μM. EtOH and PEG-300/EtOH showed a certain level neuroprotection capacity at the dilution corresponding to a 50 μM final concentration of PAN-811. PAN-811 showed good neuroprotective capacity at 1-10 μM. PAN-811 has better solubility in PEG-300/EtOH comparing to EtOH alone.

5. Conclusions

PAN-811 showed good neuroprotective capacity at 1-10 μM final concentration. PEG-300/EtOH showed very minimal interference with the assay system at dilutions corresponding to 1-20 μM of PAN-811, and is thus the best solvent for PAN-811 among the three solvents tested.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

We claim:

1. A method for the treatment of an ischemia condition in a patient in need thereof, comprising administering to said patient a compound of the formula:

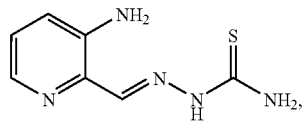

wherein the ischemia condition is an ischemia resulted from one or more of the diseases/conditions selected from the group consisting of coronary artery bypass graft surgery, global cerebral ischemia, focal cerebral infarction, cerebral hemorrhage, hemorrhage infarction, hypertensive hemorrhage, intracranial vascular hemorrhage, subarachnoid hemorrhage, hypertensive encephalopathy, carotid stenosis or occlusion, cardiogenic thromboembolism, spinal stroke, spinal cord injury, atherosclerosis, vasculitis, macular degeneration, myocardial infarction, cardiac ischemia and supraventricular tachyarrhythmia.

* * * * *